United States Patent [19]

Björnberg et al.

[11] Patent Number: 4,617,326

[45] Date of Patent: Oct. 14, 1986

[54] BACTERIA ADSORBING COMPOSITION

[75] Inventors: Sten G. Björnberg, Spånga; Wilhelm E. S. Hjertén, Upsala; Torkel M. Wadström, Knivsta, all of Sweden

[73] Assignee: Landstingens Inkopscentral Lic Ekonomisk Forening, Solna, Sweden

[21] Appl. No.: 711,715

[22] Filed: Mar. 14, 1985

[30] Foreign Application Priority Data

Mar. 14, 1984 [SE] Sweden .................................. 8401438

[51] Int. Cl.$^4$ ............................................. A61F 15/00
[52] U.S. Cl. ..................... 523/111; 128/156; 424/16; 424/27; 424/28; 604/367; 604/378; 604/383; 604/904
[58] Field of Search ............... 604/904, 383, 367, 378; 128/156; 424/16, 27, 28; 523/111

[56] References Cited

U.S. PATENT DOCUMENTS

| | | | |
|---|---|---|---|
| 3,545,442 | 9/1964 | Wicker et al. ...................... | 604/383 |
| 4,203,435 | 5/1980 | Krull et al. .......................... | 128/156 |
| 4,225,580 | 9/1980 | Rothman et al. ................... | 424/78 |
| 4,274,412 | 6/1981 | Austin ................................. | 604/904 |
| 4,287,251 | 9/1981 | King et al. .......................... | 128/156 |
| 4,335,722 | 6/1982 | Jackson .............................. | 604/904 |
| 4,354,487 | 10/1982 | Oczkowski et al. ............... | 128/156 |
| 4,373,519 | 2/1983 | Errede et al. ...................... | 128/156 |
| 4,423,101 | 12/1983 | Willstead .......................... | 128/156 |
| 4,500,585 | 2/1985 | Erickson ............................ | 604/367 |

FOREIGN PATENT DOCUMENTS

| | | |
|---|---|---|
| EP21230 | 1/1981 | European Pat. Off. . |
| EP47796 | 3/1982 | European Pat. Off. . |
| EP53936 | 6/1982 | European Pat. Off. . |
| 2271839 | 12/1975 | France . |
| WO82/3770 | 11/1982 | World Int. Prop. O. . |
| 317699 | 1/1957 | Switzerland . |
| 386067 | 1/1933 | United Kingdom . |
| 1090421 | 11/1967 | United Kingdom . |
| 1180960 | 2/1970 | United Kingdom . |

Primary Examiner—Ronald W. Griffin
Attorney, Agent, or Firm—Fred Philpitt

[57] ABSTRACT

A bacteria adsorbing composition which includes a first component comprising a powerfully hydrophobic, bacteria adsorbing, physiologically innocuous, preferably water-insoluble material, and a second component comprising a hydrophilic, liquid absorbing, physiologically innocuous material.

4 Claims, No Drawings

BACTERIA ADSORBING COMPOSITION

The present invention relates to a bacteria adsorbing composition in water-insoluble form.

It is known from European Patent Application No. 80 103 218.6 (Publication No. 0 021 230) to adsorb pathogenic microorganisms onto water-insoluble particles exhibiting hydrophobic groups by hydrophobic bonding in order to prevent or treat infections in human beings and animals. There is used in this respect swollen gel particles of a cross-linked polysaccharide in which hydrophobic groups have been arranged in side-chains projecting from the polymer skeleton. These particles are primarily intended for oral administration to treat infections in the gastro-intestinal canal, because during this passage through the canal the particles are afforded good opportunities to get into contact with bacteria present therein. The treatment of external sores with such swollen gel particles has the disadvantage that only those microorganisms which lie closest to the particles are given the opportunity to adhere thereto, this number representing only a small fraction of the total number of microorganisms present in an infected sore.

Consequently it is an object of the present invention to provide a bacteria adsorbing composition which when used in the treatment of external infections results in a more extensive removal of bacteria and other microorganisms than the prior art liquid-swollen gel particles.

It has now been found in accordance with the present invention that this can be achieved with a water-insoluble bacteria adsorbing composition which includes a first component comprising a powerfully hydrophobic, bacteria adsorbing, physiologically innocuous, preferably water-insoluble material, and a second component comprising a hydrophilic, liquid absorbing and physiologically innocuous material.

By "powerfully hydrophobic" in the context of the first component is meant that the material in question shall be capable of binding, by means of hydrophobic interaction, at least $10^7$, preferably at least $10^9$, for example fimbriated *E. coli* bacteria or *Staph. aureus* S113-83A per g dry substrate.

In the composition according to the invention the hydrophilic liquid absorbing material effects a liquid flow by suction of exudate from a discharging sore, the microorganisms accompanying this flow of liquid and being brought into contact with the hydrophobic component and bonding thereto, if they exhibit hydrophobic surface structures.

The powerfully hydrophobic, bacteria adsorbing, physiologically innocuous material is preferably water-insoluble but it can also be a water-soluble polymer in solid form which exhibits hydrophobic groups, said polymer, for instance, being negatively charged and being attached to a positively charged material, e.g. carboxymethyl cellulose.

According to one embodiment of the composition according to the invention the hydrophilic material is present in the form of one or more layers and the hydrophobic material is present in the form of one or more liquid permeable layers or is found applied to such a layer or layers, at least one layer of hydrophilic material being located externally of at least part of the hydrophobic material as seen from the surface to be treated.

The hydrophobic material may either be hydrophobic throughout or may comprise a hydrophilic substrate provided with a hydrophobic surface layer.

The hydrophobic material may comprise, for example, a hydrophobic fabric or hydrophobic non-woven fabric, or a hydrophilic fabric or non-woven fabric which has been rendered hydrophobic by a special treatment, or a hydrophobic, perforated foil. Hydrophobic woven and non-woven fabrics may be produced from synthetic fibres or the type polyamide, polypropylene and polytetrafluoroethylene fibres, or from carbon fibres. In order to obtain a hydrophobic material from a woven or non-woven hydrophilic fabric, such as woven or non-woven cotton fabric, the fabric may be treated chemically for example, in a known manner, with a compound containing hydrophobic groups, for example with a dialkylcarbamoyl chloride such as dihexadecyl-carbamoyl chloride or dioctadecyl-carbamoyl chloride.

Similarly a hydrophobic material can be obtained by binding a hydrophobic ligand chemically to a foil of hydrophilic material, e.g. to paper, cellophane or to a non-woven fabric of glass fibres.

When applied to a liquid permeable layer the hydrophobic material may, for example, be applied on a perforated foil, which can be hydrophilic or hydrophobic. Examples of materials from which such foils are produced are plastics, e.g. a polyester, metal and paper or combinations thereof.

The hydrophobic material may be fixed to the foil with the aid of a suitable adhesive for example. Examples of adhesive substances which can be used in this connection are acrylate adhesives and dispersions of vinyl acetate, ethyl acetate and latexes.

In addition to having also in this case the form of a woven or non-woven fabric, the hydrophobic material may also have a particulate form with a particle size in the range of 0.1–1000 μm.

Examples of hydrophilic, liquid absorbing physiologically innocuous materials which may be contemplated for use in the second component of the composition are tissue paper, cotton, cellulose fluff, starch, cross-linked polysaccharides, vinyl polymers and acryl polymers and a hydrophobic material treated with a hydrophilic substance.

Examples of cross-linked polysaccharides are methyl cellulose, ethyl cellulose, hydroxyethyl cellulose, dextran or starch cross-linked with the aid of a bifunctional cross-linking agent such as a bifunctional glycerol derivative of the type dichlorohydrin or dibromohydrin or the corresponding epoxide compounds obtainable by splitting-off hydrogen halide, i.e. epichlorohydrin and epibromohydrin, or a diepoxide such as 1,2-3,4-diepoxybutane. Examples of other hydrophilic polymers are acryl polymers, which may be cross-linked linked with, for instance, methylenebisacrylamide.

In order to obtain a hydrophobic material provided with a hydrophilic surface layer, substances such as dextran, starch, polyvinylpyrrolidone, polyacrylamide, ethylene glycol, polyethylene glycol, mannitol and other poly-valent alcohols, amides such as acryl amide and methacrylamide, and polyethylene oxide may be bound covalently to a hydrophobic plastics material with the aid of methods known per se.

According to another embodiment of the invention the bacteria-adsorbing composition comprises a mixture of fine particles of the two materials. In this case the particles preferably have a size within the range of 0.1–1000 μm. The mixture may be in a loose form, as a sprinkling powder, or in paste form, or may be portioned into bags or dressings comprising a fine-woven material or porous material which will retain the particles within the bag while permitting the transport of bacteria and exudate through the walls thereof.

In this embodiment the hydrophobic material is preferably a physiologically innocuous salt of a fatty acid having 6–30, preferably 10–20 carbon atoms, an alkanol, alkane or fatty acid having a melting point above 45° C., or a mixture of such substances. These substances may also have the form of particulate hydrophobic material applied to a perforated foil substrate.

A paste can be produced, for example, by mixing fine particles of the hydrophobic and hydrophilic materials with an ointment-base component suitable for the preparation of pastes, such as glycerol, a polyethylene glycol or vaseline.

According to a further embodiment of the composition according to the invention the two components are combined in a single substance comprising a dry, particulate water-swellable polymer exhibiting hydrophobic groups.

In this instance the basic polymer may comprise, for example, agarose, a vinyl or acryl polymer or a cross-linked polysaccharide of the kind mentioned above in conjunction with the hydrophobic, liquid-absorbing, physiologically innocuous water-insoluble material. Hydrophobic groups are arranged in side-chains projecting from this base polymer in a manner corresponding to that disclosed in European patent application No. 80 103 218.6. Thus, substances of the kind revealed in said European patent application, although in a dry form, may form a composition according to the invention or be incorporated therein as the hydrophobic component. Because the particles are applied as a layer to a discharging sore when they are in dry form instead of the swollen form revealed in the aforesaid patent application there is obtained a flow of liquid into the particle layer as a result of the suction of the liquid into the particles. As a result microorganisms are also transported away from the sore and penetrate the particle layer, where they adhere to the hydrophobic groups of the polymers when said microorganisms exhibit hydrophobic surface structures.

Examples of other hydrophilic base materials in particle form which can be provided with a hydrophobic surface layer and used in a composition according to the invention are particles of silica (silicon dioxide), silica gel (i.e. silicic acid which has been dehydrated to varying degrees) and water-insoluble silicates. In these compounds groups

in the surface layers of the particles can be reacted with, for example, an epoxide of the formula

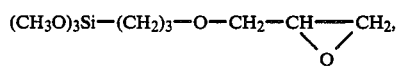

the substituent

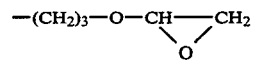

being introduced thereby, which can then be utilized to introduce a hydrophobic group R. For example, the epoxy group can be reacted with an amine or alcohol containing the hydrophobic group R, e.g. an amine $H_2N-R$. Hydrophobic groups R may also be introduced directly by reacting the particles of silicon compound with a compound $Cl_3SiR$ or $(CH_3O)_3SiR$, wherein R may be octadecyl, whereby octadecylsilyl groups are introduced into the surface layer.

According to another aspect of the present invention the hydrophobic and/or the hydrophilic material or part of said material or materials can exhibit ion exchange groups, preferably anion exchange groups. In case of hydrophobic or hydrophilic materials containing hydroxyl groups, for instance, diethylaminoethyl groups can be introduced in a manner known per se by means of 2-chlorotriethylamine hydrochloride, (vide e.g. J. Am. Chem. Soc. 78 (1956) 753). Examples of other ion exchange groups of interest in this connection are quaternary ammonium groups and carboxylmethyl groups, which likewise can be introduced in a manner known per se. The ion exchange group-containing material can, if desired, be present in a layer separate from hydrophobic and hydrophilic material lacking such groups. Moreover it can comprise ion exchange materials known per se, such as diethylaminoethyl cellulose, diethylaminoethyl dextran, diethylaminoethyl agarose, carboxymethyl cellulose, carboxymethyl dextran, carboxymethyl agarose and other basic or acidic ion exchangers, which preferably are mixed with the hydrophobic material.

The invention also relates to a process for the preparation of a bacteria adsorbing composition in water-insoluble form, which process is characterized in that a first component comprising a powerfully hydrophobic, bacteria adsorbing physiologically innocuous, preferably water-insoluble material, and a second component comprising a hydrophilic, liquid absorbing and physiologically innocuous material are combined to the formation of a product in which (a) the hydrophilic material is present in the form of one or more layers and the hydrophobic material is present in the form of one or more liquid permeable layers or is found applied to such a layer or layers, (b) the two materials are present in admixture with each other, preferably in the form of particles, or (c) the two compounds are combined chemically in one single substance, which consists of a dry, particulate, water-swellable polymer exhibiting hydrophobic groups.

In process alternative (a) it would be advantageous to place at least one layer of hydrophilic material in such a way in the product that it becomes located externally of at least part of the hydrophobic material as seen from the surface to be treated when using the product.

A product comprising a number of layers obtained according to this alternative can, if desired, be rolled up to an at least substantially cylindrical body, which can be provided with a liquid permeable cover.

The product obtained according to process alternative (b) is preferably a powder mixture but can also be, for instance, a mixture of at least one hydrophilic and at least one hydrophobic material in the form of fibre flocks and/or larger particles or pieces of soft material, the mixture preferably being encompassed by a liquid permeable cover.

The composition according to the invention is primarily intended for treating infected sores and eczema and for the removal of pathogenic microorganisms and hydrophobic side or degradation products from such microorganisms in vagina.

The composition is preferably adapted to the amount of exudate discharging from the sore, such that in the case of large quantities of exudate there is chosen a composition having a high liquid absorbing capacity while a composition of relatively low liquid absorbing capacity is preferred in the case of small amounts of exudate. For the same reason it may be found suitable during the course of treatment to change the type of composition according to the invention used, as the sore heals. In the case of sores which discharge heavily, it is therefore suitable at the beginning of the course of treatment to use, for example, a composition according to the invention which absorbs relatively large amounts of exudate, e.g. 1 g cross-linked methylcellulose or acryl copolymers, so-called super absorbent, for each $cm^2$ of infected surface mixed with approximately 1 g of a powerfully hydrophobic material, e.g. magnesium stearate or cellulose palmitate. An exudate amount of at least 20 g can be absorbed in this way for each $cm^2$ of infected area. An adsorption of $10^{12}$ bacteria/$cm^2$ infected area is fully possible when the bacteria in the sore exhibit a sufficiently hydrophobic surface structure.

In order to prevent the sore from drying out, which can have an inhibiting effect on the healing process, the absorption capacity should be reduced after a suitable length of time to, e.g. 2-4 g exudate/$cm^2$ infected area, by changing to 0.5 g solanum amylum starch/$cm^2$ infected area +0.5 g bacteria-adsorbing magnesium stearate. In the terminal stages of the healing process there is suitably used a dressing comprising a surface layer of thin perforated polyester film, 10-20 $\mu$m, coated with a thin layer of magnesium stearate. Placed inwardly of this layer is preferably an absorption body comprising several layers of cellulose tissue (0.1-0.01 g/$cm^2$ infected area). A minimal drying-out of the sore is achieved in this way while, at the same time, any bacteria remaining will be adsorbed on the surface layer. The risk of the surface layer becoming fastened in the sore during the final steps of the healing process with this type of surface is small.

The time intervals between changes of the various compositions vary between the types of sores being treated and should be capable of being correctly adapted by skilled nursing staff.

The composition according to the present invention can also be used for hygienic purposes which involves absorption of liquid which can contain bacteria. Thus the composition can be given the form of, or be incorporated in a babies' napkin, a sanitary towel or a tampon or another sanitary product containing at least one liquid absorbing material.

The invention will now be described in more detail with reference to a number of working examples.

EXAMPLE 1

A compress was prepared by immersing a cotton gauze in a 2%-by weight aqueous dispersion of dioctadecyl carbamoyl chloride and drying said gauze in an oven for 20 minutes at a temperature of 120° C. The resultant hydrophobic gauze was then laid around an absorption core comprising nine layers of cellulose tissue with two layers of hydrophobic gauze on each side of the absorption core.

EXAMPLE 2

50 parts by weight magnesium stearate of a pharmacological quality were mechanically mixed with 50 parts by weight powdered potato starch of pharmacological quality. The preparation was poured into glass jars and gammasterilized.

EXAMPLE 3

Example 2 was repeated with the exception that this time the preparation was poured into suitably sized bags or sackets made of wet strength soft paper or nonwoven polypropylene, instead of being poured into glass jars.

EXAMPLE 4

A paste was produced from the preparation according to Example 2, by mixing glycerol and the preparation in a weight ratio of 1:3.

EXAMPLE 5

Example 2 was repeated but with 50 parts by weight palmitoyl cellulose instead of magnesium stearate.

The palmitoyl cellulose was produced by reacting cellulose with palmitoyl chloride in pyridine at 80° C., whereafter ethanol was added and the product filtered and washed.

EXAMPLE 6

Potato starch of pharmacological quality was suspended in an aqueous dispersion of dioctadecyl carbamoyl chloride (approximately 2% by weight active substance), filtered-off and spread onto a plate to be dried. The dry hydrophobized starch product was pulverized.

50 parts by weight of the resultant pulverized hydrophobized starch was mixed with 50 parts by weight of a nonhydrophobized pulverulent potato starch of pharmacological quality, whereafter the mixture was filled into glass jars and gammasterilized.

EXAMPLE 7

50 parts by weight magnesium stearate of pharmacological quality were mixed with 50 parts by weight of cross-linked linked methyl cellulose or acryl copolymer, so-called super absorbent. The mixture was portioned into packages analogously with Example 3.

EXAMPLE 8

A perforated polyester foil having a thickness of 20 $\mu$m was coated with an acrylate adhesive (033-1223 from National Adhesive, England) in an amount of 5-15 g/$m^2$. While the foil was wet it was coated on both sides with magnesium stearate in powder form (particle size 0.1-100 $\mu$m). Excess magnesium stearate was removed by suction whereafter the foil was left to dry in the air.

The foil was then laid around cellulose tissue in a manner corresponding to that of the hydrophobic gauze of Example 1.

EXAMPLE 9

A compress was prepared analogous to Example 1 but using an aqueous dispersion of dioctadecyl carbamoyl chloride to which there had also been added a cationic modified copper phthalocyanine dye (Acuonium Turquoise, Liquid from AWL Scandinavia AB, Malmö, Sweden).

EXAMPLE 10

A tampon comprising partly of hydrophobated cationically active gauze prepared analogous to Example 9 and partly of cotton, one layer of gauze being placed between each layer of cotton, was prepared as follows:

On a cotton sheeting having a length of 200 mm and a breadth of 50 mm and weighing 4 g a gauze of the type set forth above having the same length and breadth as the cotton sheeting and weighing 1.0 g was placed. This sheeting was then rolled together to form a staff-shaped tampon using techniques known in the manufacturing of tampons.

The effect produced by the composition according to the invention will be described in more detail with reference to an experiment carried out on animals.

Experiment

This experiment was carried out on pigs each weighing approximately 20 kg. With the aid of a special instrument eight standardized burn sores of diameter 20 mm were inflicted on the pigs at a uniform spacing of 10 cm and four sores on each side of the spinum.

Each of the sores was infected with $10^{11}$ bacteria of type *Staphylococcus aureus* strain S-63-113A.

Subsequent to the sores becoming infected to the extent that they discharged exudate they were treated in the following manner.

The sores on the right-hand side of each pig were treated with a preparation produced in accordance with Example 3 of the present invention. The sores on the left-hand side of each pig were treated with a comparison preparation comprising potato starch of pharmacological quality. Treatment proceeded for four hours, after which time the preparation according to Example 3 above on the right-hand sores was replaced with compresses prepared in accordance with Example 1 above. The comparison potato-starch preparation on respective left-hand sores was replaced with a cotton gauze compress. This course of treatment was repeated twice at an interval of 24 hours whereafter all sores were dressed with compresses of the kind designated Absderma (LIC, Solna Sweden) until all sores were completely healed.

It was found that the right-hand sores treated with preparations according to the invention healed much more quickly than the left-hand sores treated with the comparison preparation. The difference in the healing rate is ensured at a level of 95% and relates to a decrease in the diameter of respective sores from the time of commencing treatment.

We claim:

1. A bacteria adsorbing composition in water-insoluble form which includes a first component comprising one or more liquid permeable layers of a powerfully hydrophobic, bacteria adsorbing, physiologically innocuous material comprising a woven or non-woven hydrophilic fabric, which has been rendered hydrophobic by chemical treatment with a compound containing hydrophobic groups, and a second component comprising one or more layers of a hydrophilic, liquid adsorbing, physiologically innocuous material, at least one layer of hydrophilic material being located externally of at least part of the hydrophobic material as viewed from the surface to be treated.

2. A composition according to claim 1 wherein the hydrophilic material comprises soft paper, cotton, cellulose fluff, starch, cross-linked polysaccharides, vinyl and acryl polymers, or a hydrophobic material treated with a hydrophilic substance.

3. A composition according to claim 1 wherein the first component comprises cotton fabric, which has been rendered hydrophobic by chemical treatment with a dialkylcarbamoyl chloride.

4. A composition according to claim 1 wherein the first component comprises cotton gauze which has been rendered hydrophobic by chemical treatment with dioctadecyl carbamoyl chloride.

* * * * *